United States Patent [19]
Ritter

[11] Patent Number: 5,861,149
[45] Date of Patent: Jan. 19, 1999

[54] METHODS FOR WOUND TREATMENT

[75] Inventor: Vladimir Ritter, Kiriat-Yam, Israel

[73] Assignee: Polyheal Ltd., Haifa, Israel

[21] Appl. No.: 868,950

[22] Filed: Jun. 4, 1997

[51] Int. Cl.$^6$ .................................................. A61K 31/74
[52] U.S. Cl. ...................................... 424/78.06; 514/866
[58] Field of Search ........................................ 424/78.06

[56] References Cited

U.S. PATENT DOCUMENTS

| | | | |
|---|---|---|---|
| 3,842,830 | 10/1974 | Hargest | 128/155 |
| 4,273,871 | 6/1981 | Tolnbert et al. | 435/41 |
| 4,781,921 | 11/1988 | Smith et al. | 424/81 |
| 4,889,530 | 12/1989 | Smith et al. | 604/304 |
| 5,077,058 | 12/1991 | Lapoiriere et al. | 623/11 |
| 5,092,883 | 3/1992 | Eppley et al. | 623/11 |
| 5,264,207 | 11/1993 | Bommelaer et al. | 424/69 |
| 5,356,614 | 10/1994 | Sharma | 424/45 |

FOREIGN PATENT DOCUMENTS

| | | |
|---|---|---|
| WO 94/13333 | 12/1993 | WIPO . |
| WO 96/13164 | 10/1995 | WIPO . |

OTHER PUBLICATIONS

Advertising material: "The ConvaTec Wound Care System", ConvaTec Ltd., Harrington House, Milton Rd., Ickenham Uxbridge UB10 8PU, G.B.

Ritter, et al., "The Possible Role of Synthetic Polycations in the Stimulation of Myoblast Fusion", Intercellular Communication, F. Bukauskas, Ed., Manchester Univ. Press, no date given.

Lemperle, et al., "PMMA Microspheres (Artecoll) for Skin and Soft–Tissue Augmentation, Part II: Clinical Investigations", Plastic and Reconstructive Surgery, pp. 627–634, (Sep., 1995).

Mustoe, et al., "Enhanced Healing of Cutaneous Wounds in Rats Using Beads with Positively Charged Surfaces", Plastic and Reconstructive Surgery, pp. 891–899, (May, 1992).

Advertising material: "Granuflex", Squibb Surgicare Ltd., Squibb House, 141–149 Staines Rd., Hounslow TW3 3JA.

"Worthington Enzyme Manual", Worthington Biochemical Corp., pp. 54–55.

Bonfeld, et al., "Cytokine and Growth Factor Production by Monocytes/macrophages on Protein Preadsorbed Polymers", J. Of Biomedical Materials Res., vol. 26, pp. 837–850 (1992).

Mescher, M.F., "Surface Contact Requirements for Activation of Cytoxic T Lymphocytes", J. Immun., vol. 149, pp. 2402–2405, 1992.

Bonfeld, et al., "Functional Versus Quantative Comparison of IL–1α From Monocytes/Macrophages on Biomedical Polymers", J. Biomedical Materials Res., vol. 27, pp. 1195–1199 (1993).

Epplley, et al., "Effects of a Positively Charged Biomaterial for Dermal Subcutaneous Augmentation", Aesth. Plas. Surg., vol. 18 pp. 413–416 (1994).

Hasani, et al., "Effect of Temazepam on Tracheobronchial Mucus Clearance", Thorax, vol. 47, p. 298–300 (1992).

Becquemin, et al., "Particle Deposition and Resistance in the Noses of Adults and Children", Eur. Respir. J., vol. 4, pp. 694–702 (1991).

*Primary Examiner*—Leonard Schenkman
*Attorney, Agent, or Firm*—Mark M. Friedman

[57] ABSTRACT

A method and a device for the treatment of wounds and promotion of wound healing and muscle regeneration. The method includes applying a composition including a non-biodegradable microsphere with a substantial surface charge to the subject. The device further includes a pharmaceutically acceptable carrier and a container for containing the composition and the carrier. The microspheres used in the present invention have been shown to promote wound healing and muscle regeneration both in vivo and in vitro.

12 Claims, 17 Drawing Sheets
(11 of 17 Drawing Sheet(s) Filed in Color)

Control rat

Experimental rat

Healing of wounds, treated by microspheres (control rat) and by saline (control rat) five days after injury Control rat Experimental rat

METHODS FOR WOUND TREATMENT

FIELD AND BACKGROUND OF THE INVENTION

The present invention relates to wound treatment and, in particular, it concerns a device and methods for accelerating wound healing and enhancement of muscle regeneration with microspheres as a therapeutic agent.

Wound healing is a complex process involving such factors as cells, extracellular matrix (ECM) components and the cellular microenvironment. Essentially, all wound healing involves the repair or replacement of damaged tissues. The precise nature of such repair or replacement depends upon the tissues involved, although all such processes involve certain basic principles. To illustrate these principles, cutaneous, or skin, wound healing will be described, it being understood that the discussion could also extend to all types of wound repair.

Skin has multiple layers, including keratin, epidermis and dermis. If only the epidermis is damaged, as in most minor injuries, keratinocytes migrate from the edge of wound and eventually cover it, reforming the epidermis and keratin [D. R. Knighton and V. D. Fiegel, *Invest. Radiol.*, 26:604–611, 1991].

If all skin layers are damaged or destroyed, new connective tissue, called granulation tissue, must first fill the wound space. This tissue is formed by deposition of ECM components by fibroblasts, which migrate into the wound space [D. R. Knighton and V. D. Fiegel, *Invest. Radiol.*, 26:604–611, 1991]. The deposition of these ECM components, such as collagen, is currently believed to be important for healing of the wound. Indeed, the prior art teaches that the strength of the healing wound is ultimately dependent upon collagen deposition [Haukipuro, K., et al., *Ann. Surg.*, 213:75–80, 1991]. Thus, collagen deposition must be present at a sufficiently high level to give the healing wound strength and support.

This entire multi-step process must be completed for successful wound healing. If one or more of these components is missing, healing does not take place, the skin is not repaired and the wound remains open. Such open wounds can easily become infected, further retarding the process of healing and leading to the formation of ulcers and sores on the skin. The process of wound healing is further inhibited in many patients by the presence of other complicating conditions, such as diabetes and old age. Patients with such conditions often have skin wounds which ulcerate and refuse to heal, or only heal slowly after an extended period of time has elapsed.

Various treatments have been used in order to accelerate the rate at which wounds heal. For example, U.S. Pat. No. 4,772,591 discloses a method of accelerating the rate of wound healing by applying a combination of ascorbic acid, calcium, tyrosine or phenylalanine, and anti-inflammatory substances to the wound. Similarly, U.S. Pat. No. 4,590,212 discloses a method of applying acetaminophen to the wound. Many other patents have focussed upon other methods of accelerating the rate of wound healing. However, none of these methods has proven broadly effective.

In an attempt to improve treatments for wounds, various pharmaceutical carriers have been employed to deliver chemotherapeutic agents to the wound. Such carriers are particularly required for skin wounds since they are generally either exposed to air, or covered by bandages or clothing. In either case, the therapeutic agent can easily be removed by rubbing, for example. Thus, various creams, gels and powders have been used as pharmaceutical carriers, in an attempt to overcome this problem.

One interesting group of pharmaceutical carriers employs microspheres, which are small, microscopic particles made of various materials, including plastics and long-chain carbohydrates. Many prior art applications are known for microspheres as carriers for various therapeutic agents. For example, U.S. Pat. No. 5,264,207 discloses microspheres as a carrier for a pharmaceutical or cosmetic substance. A composition containing the microspheres and the active substance is applied cutaneously, with the microspheres in effect enabling such a route of administration for the active substance. However, this reference does not teach or suggest using the microspheres themselves as a therapeutic substance.

Similarly, PCT Application Nos. WO 96/13164 and WO 94/13333 both disclose microspheres made of a material which catalyzes the production or release of certain therapeutic substances. PCT Application No. WO 96/13164 discloses polymeric nitric oxide adducts which release nitric oxide when directly applied to damaged tissue. PCT Application No. WO 94/13333 discloses particles which are chemically modified to have free radical activity in the wound environment. Again, neither reference teaches or suggests using the microspheres themselves as a therapeutic substance, without chemical modification of the microsphere material.

However, certain properties of the microspheres used as pharmaceutical carriers were shown to influence the effect of the therapeutic substance itself. For example, the activation of cytotoxic T lymphocytes by class I alloantigen immobilized on latex microspheres was studied. Although the class I alloantigen was clearly providing the stimulus itself, the extent of cell stimulation was increased by using particle sizes of 4 to 5 microns [M. F. Mescher, *J. Immunol.*, 149:2402–2405, 1992]. Such increased stimulation may demonstrate surface contact requirements for cytotoxic T lymphocytes. In other words, the optimum particle size may have increased the effect of class I alloantigen by providing an optimum surface area for cell contact. It should be emphasized, however, that these beads were still only carriers for the active substance.

Attempts have been made to exploit the apparent ability of certain particles to enhance the efficacy of active substances to promote wound healing. For example, U.S. Pat. No. 3,842,830 discloses glass microparticles which act to promote wound healing when directly applied to damaged tissue. U.S. Pat. No. 5,092,883 discloses biodegradable positively-charged dextran beads with a similar ability to promote osteogenesis and healing of soft tissue injuries. However, none of these references teaches or suggests the promotion of regeneration of muscle by administration of microspheres to the wound. Furthermore, none of these references teaches microspheres which initially promote more rapid cell metabolism and proliferation, yet which have a limited, finite effect, so that rapid cell metabolism and proliferation are not permanently induced.

Such a limited effect is especially important in promoting wound healing, which requires an initial increase in cell metabolism and proliferation, followed by a cessation of such cell activation after healing has occurred. Without an induction of such activation, wound healing will not occur. However, if cell activation does not cease after healing is substantially complete, abnormal scar formation can result, as in the formation of keloids. Thus, there must be a balance between promotion and inhibition of cell metabolism and proliferation during wound healing.

There is therefore an unmet medical need for a particulate substance which can be directly applied to damaged tissue in order to promote healing, yet which has self-limited effects and which is substantially non-toxic, and which can also promote muscle regeneration.

SUMMARY OF THE INVENTION

According to the teachings of the present invention, there is provided a method and device of treating a wound of a subject. The method includes the step of administering a composition to the wound of the subject, the composition consisting essentially of an agent capable of forming a multi-point contact with a cellular membrane, the agent being substantially non-biodegradable during the period of treatment. Preferably, the agent is a microsphere having charged surface groups. According to one embodiment, the composition consists essentially of an agent with charged surface groups, wherein the charge can be negative or positive.

According to particular embodiments of the present invention, the microsphere material is selected from the group consisting of polystyrene, derivatized polystyrene, polymethylmethacrylate (PMMA), silicone, polylysine, poly-N-ethyl-4-vinylpyridinium bromide and latex. According to certain embodiments of the present invention, the charged surface groups are selected from the charged groups consisting of polystyrene, derivatized polystyrene, sulfate, poly-N-ethyl-4-vinylpyridinium bromide, protamine, protamine sulfate, protamine salts, polylysine and carboxyl. Also preferably, the microsphere has a diameter in a range of from about 0.01 microns to about 200 microns, more preferably in a range of from about 0.1 to about 100 microns, and most preferably from about 0.1 to about 20 microns. According to another embodiment of the present invention, the composition also includes a pharmaceutically acceptable carrier for the microsphere.

According to yet another embodiment of the present invention, there is provided a method of promoting muscle regeneration in a subject, including the step of administering a composition to the subject, the composition including an agent capable of forming a multi-point contact with a muscle cell, preferably a microsphere having a surface group with a substantial charge which may be either positive or negative.

According to still another embodiment of the present invention, there is provided a device for treating a wound, including: (a) a composition including an agent being capable of forming a multi-point contact with a cellular membrane and a pharmaceutically acceptable carrier in which the agent is substantially insoluble; and (b) a container for containing the composition. As exemplified, the carrier is preferably selected from the group consisting of aqueous medium, aerosol carrier, ointment and bandage.

According to yet another embodiment of the present invention, there is provided a device for promoting muscle regeneration, including: (a) a composition including an agent being capable of forming a multi-point contact with a cellular membrane and a pharmaceutically acceptable carrier in which the agent is substantially insoluble; and (b) a container for containing the composition.

The method of the present invention may also be used cosmetically, to prevent excess scar formation in a cut or other wound to the skin such as the skin of the face, and to treat acne.

DETAILED DESCRIPTION

The present invention relates to a device and a method for promoting wound healing by using microspheres. Unexpectedly, microspheres of the particular size range described herein are able to promote wound healing without the further addition or inclusion of any drug or other therapeutic substance. Indeed, as described below, these microspheres do not degrade or undergo other chemical alteration in order to produce their therapeutic effect.

The structure of these microspheres includes a core material and at least one type of charged surface group which is present at least on the exterior of the microsphere. Examples of materials include long-chain polymers such as polystyrene, latex, poly-α-alanine, polymethylmethacrylate (PMMA), silicone and derivatized polystyrene. Examples of surface groups include sulfate, poly-N-ethyl-4-vinylpyridinium bromide, protamine, protamine sulfate, protamine salts, polylysine, carboxyl and polystyrene. These surface groups may be present as part of the core material, or may be added later by such chemical processes as derivatization of the long-chain polymer. Hereinafter the term "derivatization" refers to the process of chemically altering, modifying or changing a molecule or a portion thereof. The microspheres produced from the polymer should be substantially insoluble in aqueous media, instead forming a suspension or dispersion in such media.

In order to further clarify the parameters of the present invention, a number of terms should be defined. Hereinafter, the term "wound" includes any injury to any portion of the body of a subject including, but not limited to, acute conditions such as thermal burns, chemical burns, radiation burns, burns caused by excess exposure to ultraviolet radiation such as sunburn, damage to bodily tissues such as the perineum as a result of labor and childbirth, including injuries sustained during medical procedures such as episiotomies, trauma-induced injuries including cuts, those injuries sustained in automobile and other mechanical accidents, and those caused by bullets, knives and other weapons, and post-surgical injuries, as well as chronic conditions such as pressure sores, bedsores, conditions related to diabetes and poor circulation, and all types of acne. Areas of the body which can be treated with the present invention include, but are not limited to, skin, muscle and internal organs. Hereinafter, the term "subject" refers to a human or lower animal on whom the present invention is practiced.

Hereinafter, the term "promoting" includes accelerating and enhancing. Hereinafter, "reducing scarring" includes preventing or decreasing excess scar formation such as keloids and hypertrophic scars, as well decreasing the extent of scar tissue formation both externally such as on the skin of the subject, and internally such as adhesions. Finally, it should be noted that the method of the present invention may also be used cosmetically, to prevent excess scar formation in a cut or other wound to the skin such as the skin of the face, and to treat acne. In a cosmetic sense, the term "excess scar formation" includes any scarring which is cosmetically undesirable or unacceptable.

Although the discussion below refers to specific types of microspheres, it should be noted that this is not intended to be limiting in any way. It will be appreciated to those skilled in the art that these microspheres, more generally described as "agents", can be beads, particles or globules which are either solid or hollow. In preferred embodiments of the present invention, these agents are dispersed in a pharmaceutically acceptable carrier medium in which the agents are substantially insoluble, as a suspension in aqueous medium for example, or in a non-aqueous medium such as an ointment, aerosol spray, or a bandage which may be occlusive or non-occlusive. The shape of the agents can be regular, such as spherical or elliptical, or regular non-spherical shapes; or the shape of the particles can be non-regular, so that the surface is not a single continuous curve or so that the surface is not smooth.

Furthermore, the agents can be a mixture of different polymers and can also be a mixture of different particles, beads or globules of different sizes. The agents can also have pores of different sizes.

By way of example, the long-chain polymer forming the agents, such as poly-β-alanine, can be cross-linked, which particularly favors the spherical shape of a microsphere, although such a shape can be obtained without cross-linking. An example of a method of manufacture for a cross-linked poly-β-alanine microsphere is given in U.S. Pat. No. 5,077,058, although it should be noted that this material would require further derivatization to obtain an overall surface charge of the microsphere.

Alternatively, the particles can have chaotic irregular forms, particularly if the polymer is not cross-linked. The particle can have any form, such as coiled, globular, extended and random coil. Preferably, the polymer should not be biochemically reactive and should be non-biodegradable. Most preferably, the polymer is non-biodegradable substantially during the treatment period, so that it would remain undegraded during the period required for healing of the wound. Hereinafter, the term "non-biodegradable" refers to agents which are not biodegradable during the treatment period, which is the period required for treatment of the wound.

At the very least, the agents should have the following properties:

1. They should be capable of forming multi-point contacts with cells or portions of cells thereof, such as the outer cell membrane and molecules on this membrane;
2. They should be able to promote wound healing without significant chemical alteration or degradation; and
3. They should be substantially insoluble in aqueous media such as bodily fluids, and instead should form a suspension.

These characteristics are important because as further discussed below, the effect of the agents of the present invention appears to be directly linked to the formation of multi-point contacts between the material of the agents and a portion of the cell such as the outer cell membrane, thereby forming an adherent surface for the cells to attach to. Such multi-point contacts are possible with many different polymers which permit charged groups to be accessible for interaction with molecules and portions of the outer cell membrane. Thus, although the description below focuses on one type of agent, microspheres, it is understood that the present invention covers any material capable of forming such multi-point contacts.

As noted above, preferably the microsphere has a diameter in a range of from about 0.01 microns to about 200 microns, more preferably in a range of from about 0.1 to about 100 microns, and most preferably from about 0.1 to about 20 microns. Without desiring to be bound by any mechanism, it should be noted that these preferred ranges are the best size for enabling uptake of the microspheres by macrophages infiltrating the wound area. The microspheres appear to actually attract and activate the macrophages through contact with at least a portion of the macrophages, probably the molecules of the outer cell membrane of the macrophage. The anti-inflammatory and anti-bacterial effects observed for the microspheres are thus presumably indirect effects, obtained through the activation of the macrophages or other cells.

Another important property of the microspheres is the charge of the surface groups. The overall charge carried by certain preferred examples of microspheres was measured as a Z or zeta potential by electrophoretic mobility (milliVolts) by a ZetaMaster (Malvern Instruments, United Kingdom). The range of Z potentials measured in certain embodiments exemplified herein was from −29.58 mV to −79.76 mV. Hereinafter, the term "charged" refers to a Z potential with an absolute value of at least about 1 mV, and preferably of at least about 10 mV, whether negative or positive.

The microspheres in the suspensions tested did not aggregate, coalesce, clump or undergo irreversible caking. Although the microspheres did settle somewhat over time, they were easily resuspended with gentle agitation.

BRIEF DESCRIPTION OF THE DRAWINGS

The file of this patent contains at least one drawing executed in color.

The invention is herein described, by way of example only, with reference to the accompanying drawings, wherein.

DESCRIPTION OF THE PREFERRED EMBODIMENTS

Figure 1:
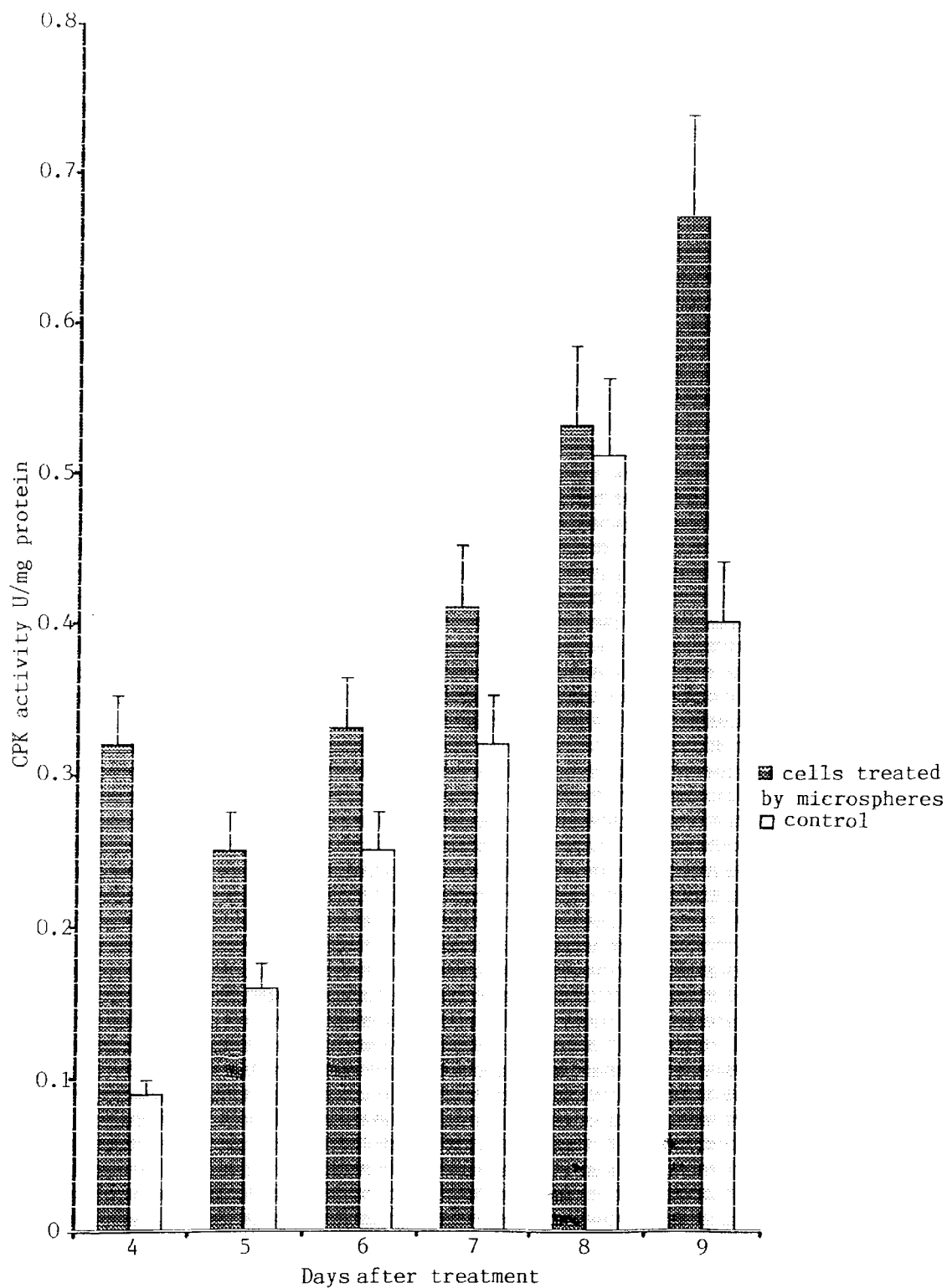
FIG. 1 is a graph showing the ability of the microspheres of the present invention to increase creatine phosphokinase activity.

The present invention is exemplified herein by the use of microspheres which can be used to promote wound healing in general, as well as muscle regeneration. Wound healing and muscle regeneration both involve the repair of damaged tissue and the replacement of missing tissue. The migration and proliferation of specific types of cells must occur in an orderly and structured manner, which can be easily differentiated from the unrestrained growth of malignant tissues such as solid tumors. In particular, cells involved in wound healing and muscle repair must first become activated in order to perform their required roles in the healing process. Although the exact mechanism is not known, the orderly, structured cell growth in proliferation which occurs in wound healing clearly demonstrates the presence of a highly organized regulatory process.

As demonstrated in the Examples given below, the microspheres of the present invention do not appear to interfere with this complex, organized and structured process, since these microspheres clearly only quicken the pace of the overall healing process, as well as of specific steps within that process. However, unexpectedly the microspheres of the present invention do not cause the cells to exhibit a state of continuous, unrestrained metabolic activation, indicating that normal regulatory processes are not affected. Thus, the microspheres of the present invention do not cause unrestrained cellular activation.

Without limiting the present invention to a particular mechanism, the addition of microspheres with negatively charged groups may have a therapeutic effect on wound healing by serving as an additional surface for the attachment and plating of cells. One hypothesis for the efficacy of the microspheres of the present invention is that the negatively charged groups enable the creation of multiple links between the solid surface of the microsphere and the cell membranes, which represent multi-point contacts between the material of the microsphere and the cell membrane. The formation of these links causes changes in the distribution and state of membrane ligands, cytoskeletal reorganization, activation of intracellular signal transduction and other biochemical changes, eventually leading to activation of the cell. Cell activation then leads to cell proliferation and production of growth factors, and of collagen and other components of the extracellular matrix. It should be noted that the present invention need not rely on any particular mechanism, since as demonstrated below, these microspheres clearly had a beneficial effect for wound treatment and healing in vivo.

A number of different types of microspheres were tested in the Examples below. These microspheres were made of polystyrene, either with carboxyl or amino surface groups or without additional surface groups. The diameters of the microspheres ranged from about 0.1 to about 20 microns. The zeta potential of certain microspheres was also tested and demonstrated that the size of the sphere and the type of surface groups clearly had an effect on the amount of overall charge carried by each microsphere, which could have important effect on the ability of the microsphere to promote wound healing.

Although certain specific types of microspheres are illustrated, it is understood that many other related types of microspheres could be used if the following characteristics were fulfilled.

1. They should be capable of forming multi-point contacts with cells or portions of cells thereof;
2. Their mechanism of action should not require chemical alteration or degradation; and
3. They should be substantially insoluble in aqueous media such as bodily fluids, and instead should form a suspension.

Other preferable attributes include the following. First, the microspheres should preferably be made from material which is non-biodegradable during the treatment period, most preferably polystyrene. Second, the microspheres should preferably carry a substantial charge, more preferably an overall negative charge. Although the size of the microspheres is less critical, preferably the microspheres should be from about 0.1 to about 20 microns in diameter. Preferably, the microspheres should be derivatized with carboxyl surface groups, although other negatively charged groups may also be used. Thus, these types of microspheres are given for illustrative purposes only and are not meant to be limiting in any way.

The principles and operation of microspheres according to the present invention may be better understood with reference to the Examples, drawings and the accompanying description.

EXAMPLE 1

Effect of Microspheres on Creatine Phosphokinase

The microspheres of the present invention clearly induced an initial increase in creatine phosphokinase (CPK) activity of cultured myoblasts, as shown in FIG. 1. However, after eight days, the untreated and treated cells both demonstrate the same level of CPK activity, indicating that the induction of increased CPK activity by the microspheres of the present invention is temporary. The experimental method was as follows.

A primary culture of rat embryo skeletal muscle was prepared as described by Freshney [R. J. Freshney, *Culture of Animal Cells*, Willey, 1986, p. 117, 170–172]. Briefly, the muscles were dissected tree of skin and bone and desegregated by warm trypsinization (0.25% trypsin at 36.5° C.). Contamination by fibroblasts was reduced by preplating cells for 1 hour in an incubator with 5% $CO_2$, 37° C., since fibroblasts adhere to tissue culture plates first. Myoblasts were then seeded on 35 mm Petri dishes at a concentration of 50,000 cells per ml with 2 ml of media (Dulbecco modified Eagle medium: medium 199 at a 1:4 ratio), enriched by antibiotics, 10% vol/vol horse serum and 4% vol/vol chick embryonic extract. The chick embryonic extract was prepared from 10 day-old chick embryos according to R. J. Freshney, *Culture of Animal Cells*, Willey, 1986. The antibiotics included amphotericin and gentamicin, diluted as 1:1000 from the standard initial concentration of 2.5 mg/ml. After 24 hours, the media was decanted and replaced with new media containing 20% vol/vol foetal horse serum and 1% vol/vol chick embryonic extract.

The cultured cells were then either treated with microspheres, starting at the time of plating, in media for 4–8 days or with media alone. The microspheres were either carboxylated polystyrene of 1, 2 or 4.5 microns in diameter, or polystyrene alone at 4.5 microns in diameter. The concentration of microspheres was either $10^6$ or $10^7$ per ml of media, with similar results obtained for both concentrations (not shown). After 4, 5, 6, 7 or 8 days of treatment, creatine phosphokinase activity was measured by a standard assay ("Creatine Kinase", *Worthington Enzyme Manual*, Worthington Biochemical Corporation, Freehold, N.J., USA, 1972, pp. 54–55). Results are shown in FIG. 1, as Units of CPK activity per mg of total cellular protein.

FIG. 1 clearly demonstrates the ability of the microspheres of the present invention to induce an initial increase of creatine phosphokinase activity, as compared to control cells. After 4 days of treatment, microsphere-treated cells show an initial increase of CPK activity as compared to control cells. This increase is particularly pronounced at days 5 and 6 of treatment. However, by day 7, CPK activity in control cells is beginning to achieve parity with that of microsphere-treated cells. By day 8, both control and microsphere-treated cells show similar levels of activity. Clearly microspheres promoted an initial increase of CPK activity in myoblasts, which leveled off after 8 days of treatment. Such increased CPK activity is correlated with biochemical maturation of myogenic cells. Thus, the microspheres promoted biochemical maturation of the cultured myoblasts.

EXAMPLE 2

Effect of Microspheres on Cell Proliferation and Fusion

The microspheres of the present invention were demonstrated to induce an initial increase in both cell proliferation and myoblast fusion, as compared to control (untreated) cells, as shown below.

Primary cultures of rat myoblasts were prepared as described in Example 1 above, except that the cells were grown on cover slips. Treated cells were incubated with microspheres in media, as further described below, while control cells were only given media.

To determine the extent of cell proliferation, cells were fixed in ethanol/acetic acid (3:1) and then stained by hematoxilin-eosin. The stained cells were then counted in a light microscope. The mitotic index was calculated as the proportion of cells in mitosis counted per 1000 cells.

For the examination of cell proliferation, polystyrene microspheres which had sulfate surface groups were used, with a diameter of 0.18 microns, and a concentration of $10^7$ microspheres/ml of media. A 20-fold increase in the mitotic index was observed after treatment for 24 hours with microspheres as compared to control cells. Specifically, the mitotic index of control cells was 1.25±0.7%, while that of microsphere-treated cells was 24.6±1.0%. Thus, clearly microspheres promoted a large increase in the mitotic index of the myoblasts.

The effect of microspheres on myoblast fusion was also examined. Results are given in Table 1. Generally, cells treated with microspheres exhibited about 150% fusion rate as compared to controls. However, the extent of this effect depended upon the type of microspheres and the length of treatment.

The types of microspheres tested are given in Table 1. The diameter of the microspheres is given in microns under "Diameter". The surface groups on the polystyrene beads are given under "Surface Group". Polystyrene beads without any further derivatization are "polystyrene". Beads derivatized with either carboxyl or amino surface groups are described as "carboxy" and "amino", respectively. The concentration of beads is given as number of beads per ml of media under "Conc."

Cells were prepared, fixed and stained as for determining the rate of proliferation of myoblasts, described above. Cells were initially plated at the density given in Table 1 as cells per ml media, under the column "Initial Cells". The measurements of myoblast fusion were made after the given number of days after treatment under "Days after Treatment".

The extent of fusion is calculated as the proportion of nuclei within multinuclear cells, or myosimplasts, related to the total amount of nuclei within the microscopic field, given as "Proportion of Fusion" for microsphere treated cells, and "Control Fusion" for control, untreated cells. At least 400 nuclei were counted for each experimental condition. The ratio of the extent of fusion in microsphere treated cells and control, untreated cells is given as "Relative Effect". If no value is given for a particular slot in Table 1, the value is the same as that in the row above.

TABLE 1

Effect of Microspheres on Fusion of Myoblasts

| Diameter | Surface Group | Conc. | Initial Cells | Days After Treatment | Proportion of Fusion | Control Fusion | Relative Enhancement |
|---|---|---|---|---|---|---|---|
| 0.22 | polystyrene | $10^7$ | $3 * 10^4$ | 6 | 0.75 ± 0.06 | 0.58 ± 0.10 | 1.29 |
|  |  |  |  | 7 | 0.82 ± 0.09 | 0.64 ± 0.09 | 1.28 |
| 0.49 |  |  |  | 6 | 0.86 ± 0.06 | 0.58 ± 0.10 | 1.48 |
|  |  |  |  | 7 | 0.91 ± 0.07 | 0.64 ± 0.09 | 1.57 |
| 0.91 | carboxy | $10^8$ | $5 * 10^5$ | 5 | 0.84 ± 0.06 | 0.64 ± 0.09 | 1.31 |
|  |  |  |  | 4 | 0.63 ± 0.09 | 0.51 ± 0.06 | 1.23 |
| 1.12 | amino |  | $3 * 10^4$ | 6 | 0.69 ± 0.15 | 0.58 ± 0.10 | 1.18 |
|  |  |  |  |  | 0.73 ± 0.08 | 0.58 ± 0.10 | 1.25 |
| 2.01 | carboxy | $10^7$ | $5 * 10^5$ | 5 | 0.84 ± 0.06 | 0.64 ± 0.09 | 1.31 |
|  |  |  |  | 4 | 0.63 ± 0.06 | 0.51 ± 0.06 | 1.23 |
| 4.58 |  | $10^6$ |  | 5 | 0.72 ± 0.09 | 0.64 ± 0.09 | 1.12 |
|  |  |  |  | 4 | 0.67 ± 0.09 | 0.51 ± 0.09 | 1.31 |
| 10.85 |  |  |  | 5 | 0.68 ± 0.08 | 0.64 ± 0.09 | 1.06 |
|  |  |  |  | 4 | 0.60 ± 0.10 | 0.51 ± 0.09 | 1.17 |

As can be seen from Table 1, all of the different types of microspheres promoted myoblast cell fusion, although the extent of the effect depended upon the diameter of the microsphere, the surface group on the microsphere, the number of days after treatment and the concentration. Myoblast fusion occurs when muscle tissue is formed during embryogenesis, and is also a very important step in muscle regeneration and repair of damaged muscle tissue. Thus, the ability of microspheres to promote such fusion clearly indicates the potential of these microspheres to promote muscle regeneration, as demonstrated in Example 5 below.

EXAMPLE 3

Effect of Microspheres on Collagen Synthesis and Deposition

As noted above in the Background section, collagen synthesis and deposition is an important step in the process of wound healing. Furthermore, the amount of collagen deposited in the wound is an important determinant of wound strength. Thus, although the microspheres of the present invention clearly have a variety of effects on different cell types, as demonstrated in the preceding and following Examples, clearly one important determinant of the ability of a composition to promote wound healing is its effect on collagen synthesis and deposition.

Figure 2A:
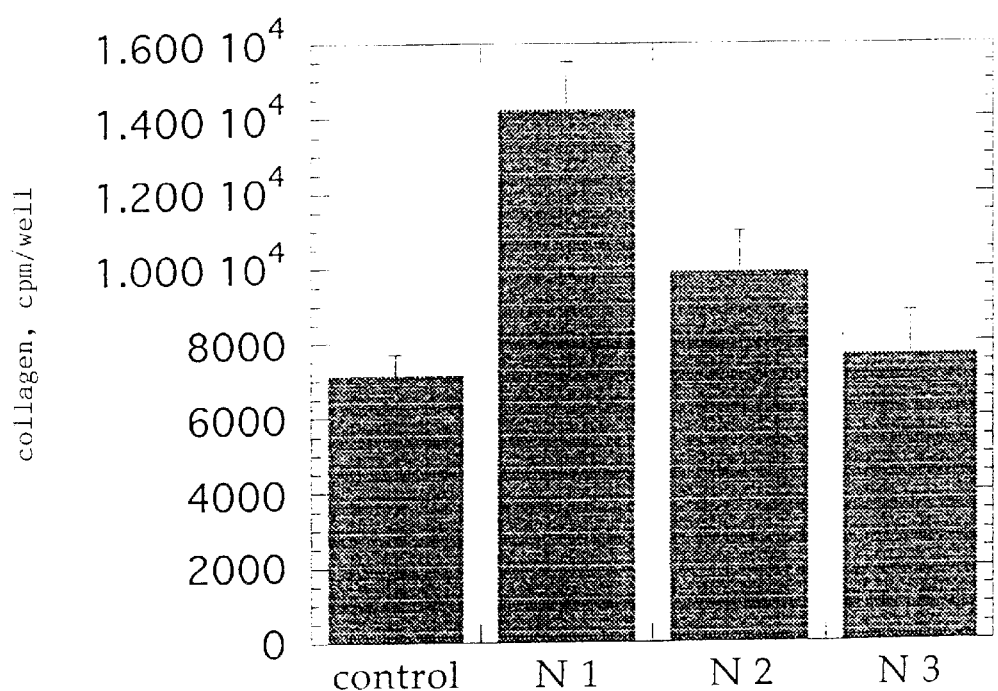
FIG. 2 is a plot illustrating the effect of the microspheres of the present invention on collagen synthesis.
Figure 2B:
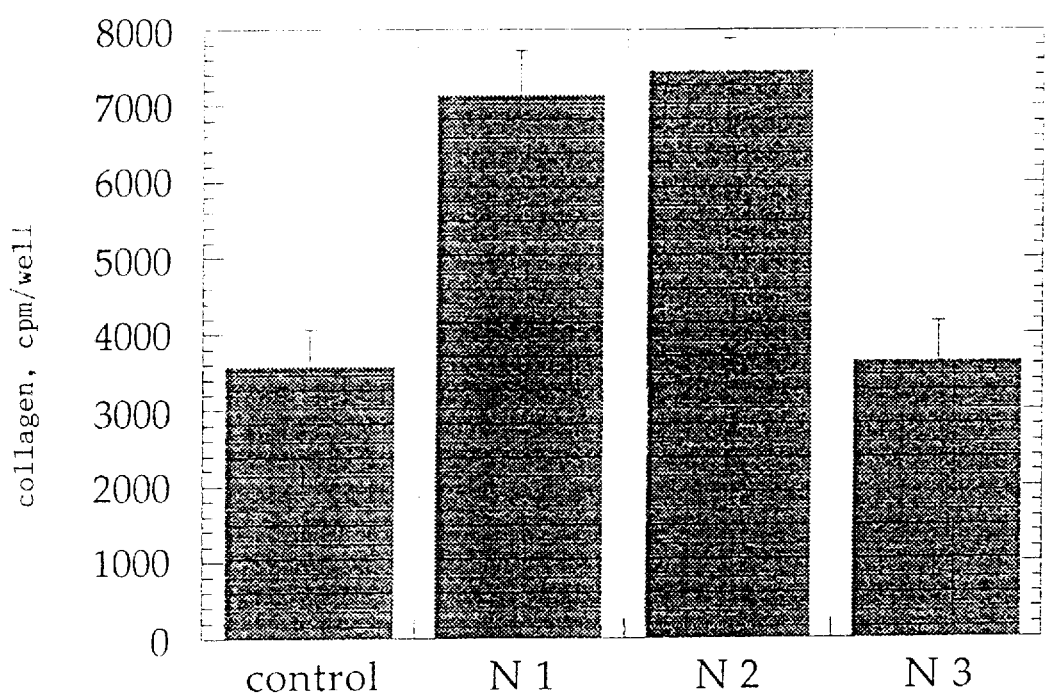

As shown in FIGS. 2A and 2B, the microspheres of the present invention clearly promote collagen synthesis by cultured fibroblasts. The largest effect is seen with Type I and Type II microspheres. Type I microspheres had a diameter of 4.5 microns, was made of carboxylated polystyrene and had a Z potential of about −29.96 mV. Type II microspheres had a diameter of 0.49 microns, were made of polystyrene alone and had a Z potential of about −34.5 mV. Type III microspheres had a diameter of 1.0 microns, were made of carboxylated polystyrene and had a Z potential of about −53.34 mV. The experimental method was as follows.

Foreskin fibroblast cultures were grown in 75 cm² plastic flasks (Corning Glass Works, Corning, N.Y.) in Dulbecco's modified Eagle medium (DMEM) containing 4.5 mg/ml glucose supplemented with 10% vol/vol fetal calf serum, 2 mM L-glutamine, 50 µg/ml gentamycin sulfate and 2.5 mg/ml amphotericin B. The cultures were incubated at 37° C. in 5% $CO_2$ until confluent. Fibroblasts were harvested using 0.25% trypsin/0.05% EDTA solution and subcultured in 24-well plates at a density of 200,000 cells/well with the same media for 24 hours, at which time treated cells were incubated with Type I, II or III microspheres. Control cells were incubated with media alone.

Collagen synthesis was measured as follows. The cultured fibroblasts were preincubated in DMEM supplemented with 0.5% dialyzed fetal calf serum for 24 hours. Cells were labeled with 3 µCi 2,3-³H-proline or 3,4-³H-proline solution containing β-aminopropionitrile fumarate (BAPN) at a final concentration of 100 µM, in the presence (FIG. 2A) or absence (FIG. 2B) of 1 0 µM ascorbic acid as indicated. Ascorbic acid promotes collagen synthesis in fibroblasts and is an important stimulation factor.

After 24 hours of incubation the reaction was terminated and collagen was extracted from each well by the addition of 30 µl cold acetic acid (0.5M) containing pepsin (final concentration 0.5 mg/ml), followed by gentle shaking at room temperature for 4 hours. After centrifugation, the cellular debris was discarded and 80 µl of collagen solution in 0.5M acetic acid was added to each supernatant, with a final collagen concentration of about 200 mg/mi. Collagen was precipitated from each supernatant by the addition of 0.4 ml of 5.2M NaCl solution in 0.5M acetic acid. After standing for 2 hours, precipitated collagen was separated by centrifugation for 15 minutes at 15,000 rpm. Next, the pellet was resuspended in 750 µl of 10 mM TRIS buffer, pH 7.4 containing 1M NaCl. Collagen was precipitated by the addition of 750 µl TRIS buffer, pH 7.4 containing 5M NaCl. After 2 hours the collagen was separated by centrifugation, redissolved in 0.5M acetic acid and each sample was measured in a scintillation counter. Results are shown in FIGS. 2A and 2B, given as cpm per well. Data presented are an average of quadruplicate samples.

Both Type I and Type II microspheres were able to stimulate collagen synthesis above the level seen in control (untreated) fibroblasts, both in the presence (FIG. 2A) and absence (FIG. 2B) of ascorbic acid. Type I microspheres had a greater effect relative to Type II microspheres in the presence of ascorbic acid, although both types had a similar effect in the absence of ascorbic acid. Type III microspheres did not have a detectable effect on collagen synthesis either in the presence or absence of ascorbic acid.

One particularly interesting finding is that both Type I and Type II microspheres had an effect, while Type III microspheres did not, indicating that the specific size and material of the microspheres is important. Furthermore, both Type I and Type II microspheres elicited an effect even in the absence of ascorbic acid, indicating that these two types of microspheres can potentiate collagen synthesis even in the absence of other stimulatory factors. Thus, clearly both Type I and Type II microspheres have a substantial stimulatory effect on collagen synthesis.

EXAMPLE 4

Effect of Microspheres on Myoblast Shape

Primary cell cultures of rat myoblasts were prepared as described in Example 1 above. Cells were then incubated with polystyrene microspheres (treated cells) or without (control cells) for 48 hours. Cells were then fixed in 1% glutaraldehyde in phosphate buffered saline for 1–4 days, and rinsed in PBS. Cells were then transferred to a solution of 1% tannic acid and 1% guanidine HCl(1:1 ratio) in PBS for 1 hour. Specimens were post-fixed in 1% $OsO_4$ for 1 hour and dehydrated in graded ethanol and Freon 113 at room temperature. Specimens were then mounted on slides, coated with gold and examined in a JEOL T-300 scanning electron microscope at 2 kV.

Figure 3A:
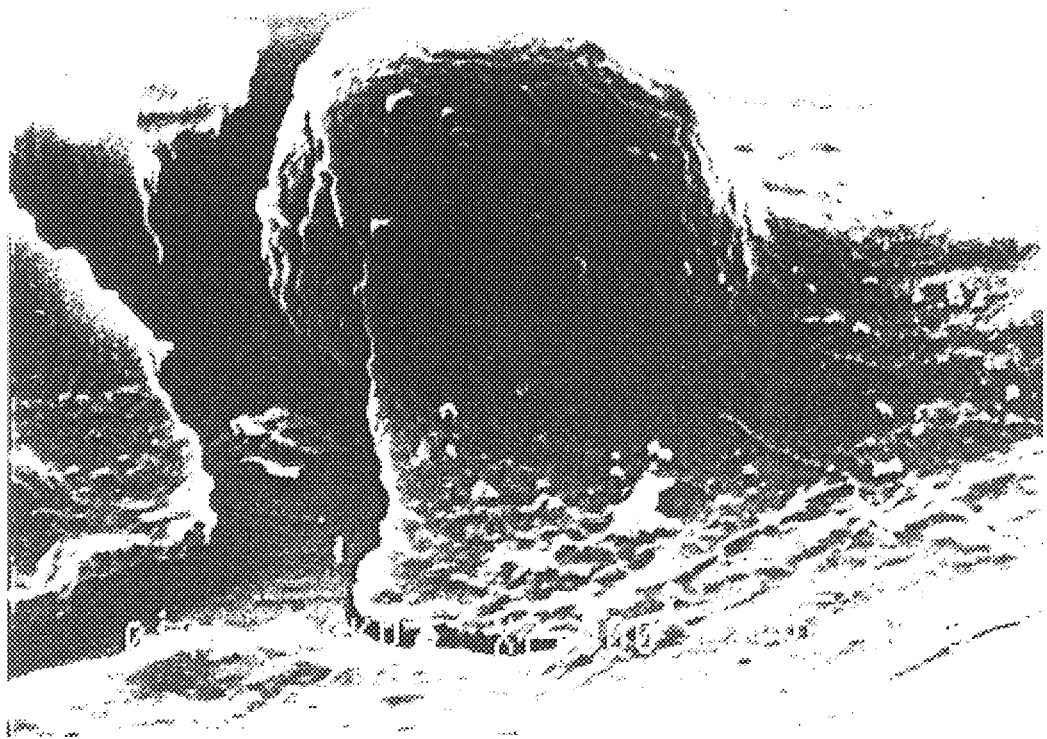
FIGS. 3A–3C illustrate the effect of the microspheres of the present invention on myoblast shape.
Figure 3B:
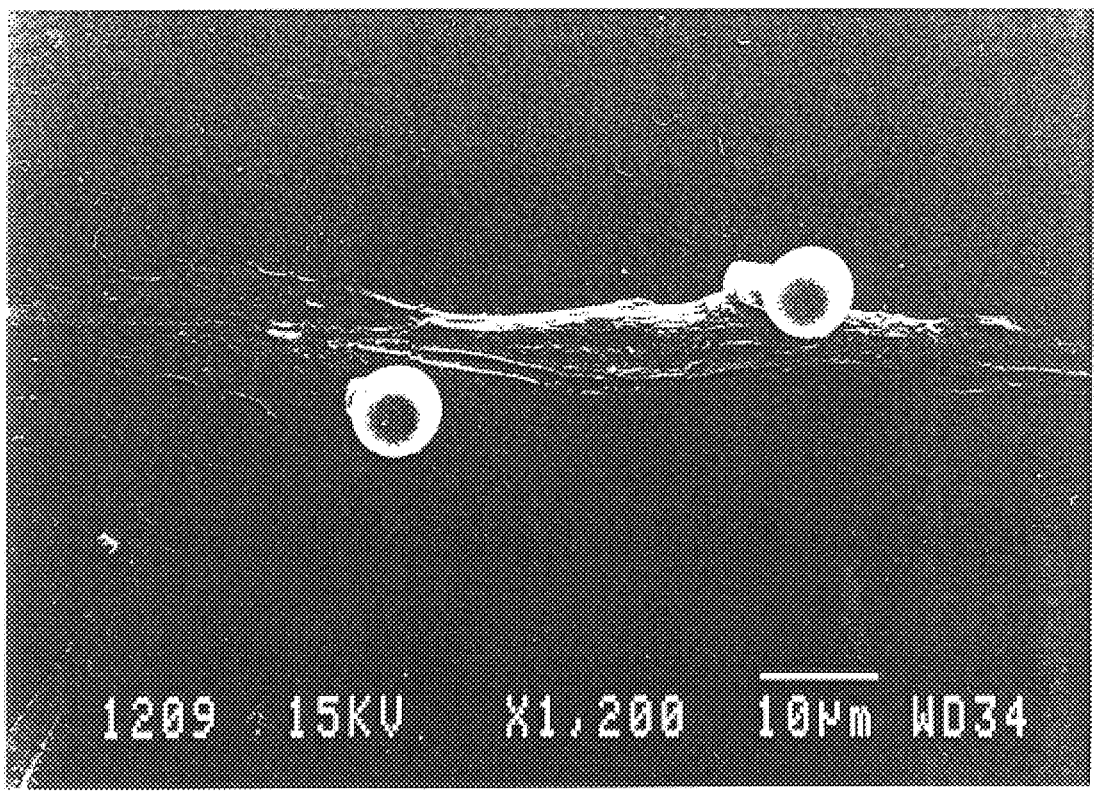
Figure 3C:
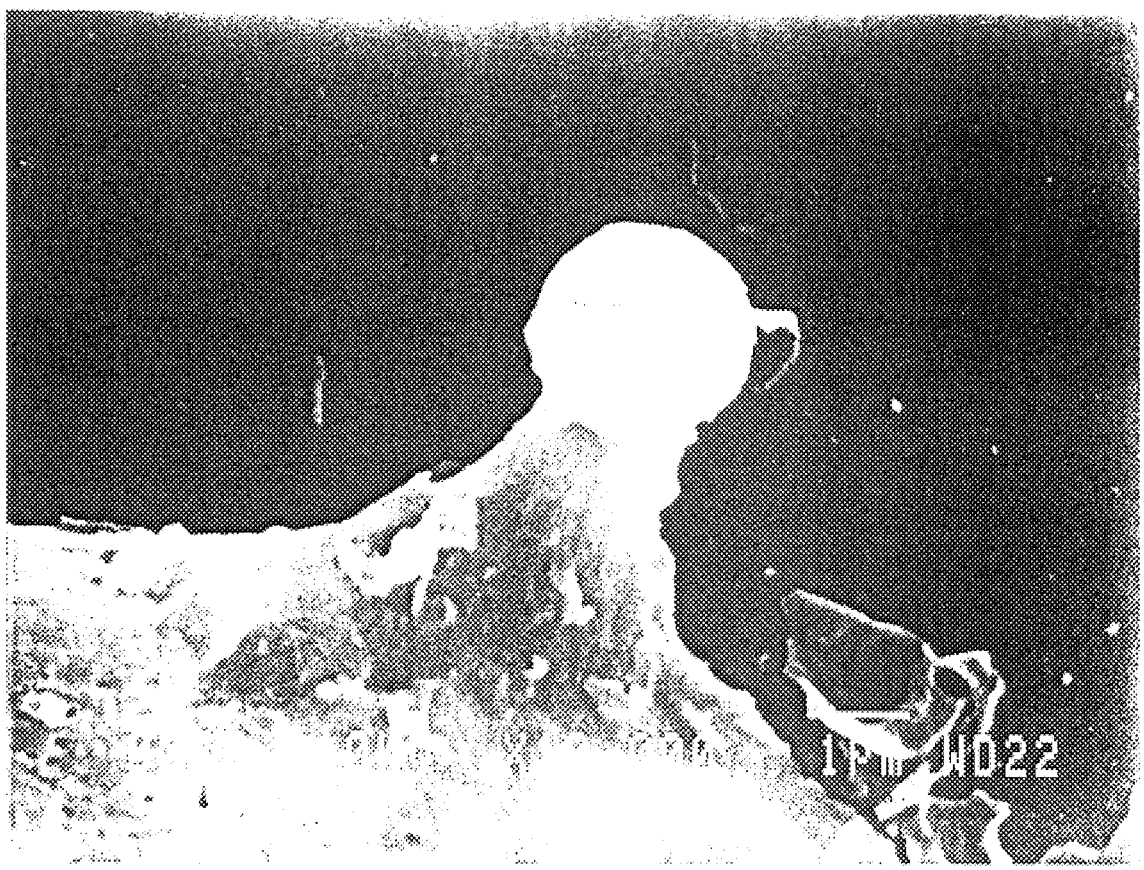

FIGS. 3A–3C illustrate the effect of the microspheres of the present invention on myoblast shape. The cell in FIG. 3A has grown over the microsphere, so that part of the cell surface is convex rather than flat. FIGS. 3B and 3C show cells extending pseudopodia from a portion of the cell on which the microsphere rests. The pseudopod of the cell in FIG. 3C is particularly pronounced, showing that the microspheres clearly influence myoblast shape. Furthermore, the formation and extension of a pseudopod clearly requires changes in the cytoskeletal structure, demonstrating that the microspheres also affect the cytoskeleton of the cell. The formation of such pseudopodia may be important for the migration of cells into the wound area. Thus, the stimulation of such pseudopodia by the microspheres indicates their ability to promote another important step in the wound healing process.

EXAMPLE 5

Device and Method for Application

The following description is a general device and method for application of the agents for wound healing. The agents, such as microspheres, are preferably applied repeatedly to the wound to be treated. The frequency of application, and the concentration applied, is dependent on the severity of the symptoms and on the responsiveness of the subject to the treatment. Persons of ordinary skill in the art can easily determine optimum concentrations, dosing methodologies and repetition rates. In the present study, the microspheres were applied to the wound to be treated about once per day, although of course other application rates are possible.

The method includes the step of administering the agents such as microspheres, in a pharmaceutically acceptable carrier in which the agents arc substantially insoluble, to a subject to be treated. Examples of pharmaceutically acceptable carriers include aqueous media for a suspension of agents, non-aqueous media such as ointments, creams and aerosol-forming material, as well as bandages soaked in, or otherwise containing, media with the agents. The bandages can be occlusive or non-occlusive. In any case, the agents which are in a pharmaceutically acceptable carrier can be described as a dispersion of agents.

The agents are administered according to an effective dosing methodology, preferably until a predefined endpoint is reached, such as the absence of clinical symptoms in the subject. The closure of the wound to be treated is an example of such an endpoint.

The device of the present invention includes a composition with one or more agents and a pharmaceutically acceptable carrier for the agents, and a container for containing the composition. Examples of suitable containers include aerosol-dispersing pumps and spray cans. One of ordinary skill in the art could easily select suitable containers for the composition.

Regardless of the particular device used, the agents, such as microspheres, are preferably applied in a two step procedure. The microspheres are first applied in a dispersion to the wound, by dripping, spraying, painting, washing or by any other suitable method of topical application. Preferably, 30 sec to 2 minutes are allowed to elapse before the second step, in order to allow the microspheres to form initial contact with the wound. Preferably, the second step includes applying an occlusive or non-occlusive bandage, or other suitable covering soaked in the liquid suspension containing the microspheres, to the wound. This substantially reduces or eliminates absorption of the microspheres by the bandage or covering. This method was used both in rats and humans for wound healing, as described in the Examples below.

The microspheres in the suspension did not aggregate, coalesce, clump or undergo irreversible caking. Although the microspheres did settle somewhat over time, they were easily resuspended with gentle agitation.

EXAMPLE 6

Promotion of Wound Healing in Rats by Microspheres

As noted above in Examples 1–4, the microspheres of the present invention promote various in vitro cell processes which are important for wound healing. However, in vitro and in vivo effects do not always correlate. Therefore, in vivo experiments were performed to assess the ability of the microspheres to promote wound healing in rats. As shown in FIGS. 4A–4D, the microspheres of the present invention clearly promote wound healing in rats. FIG. 5 is a graph of the rate at which the wound area decreases, showing that the microspheres of the present invention increase the rate at which such a decrease occurs. Finally, Table 2 shows that the microspheres promote muscle regeneration in rats. The experimental method was as follows.

Male Wistar rats, weighing between 300 and 400 g, were anesthetized by nembutal (5 mg/kg of body weight). An excision injury to the lateral parts of the Tibialis anterior muscle was performed as follows. First, a longitudinal incision was made in the skin to expose the Tibialis anterior muscle. Next, the partial excision of this muscle was made by a transverse cut of the muscle fibers, along about half of the muscle width. The excised piece was then cut out of the muscle, leaving a gap of about 5 mm by 5 mm in the muscle. In all rats the same amount of excised tissue (80±10 mg) was removed from precisely the same location in the muscle. The wound area was then dressed with 2 micron polystyrene microspheres in saline for treated rats, and saline alone for control rats. The wound area was measured for between 3 and 15 days Following injury.

Figure 4A:
FIGS. 4A–4D illustrate the ability of the microspheres to promote wound healing in rats.
Figure 4B:
Figure 4C:
Figure 4D:
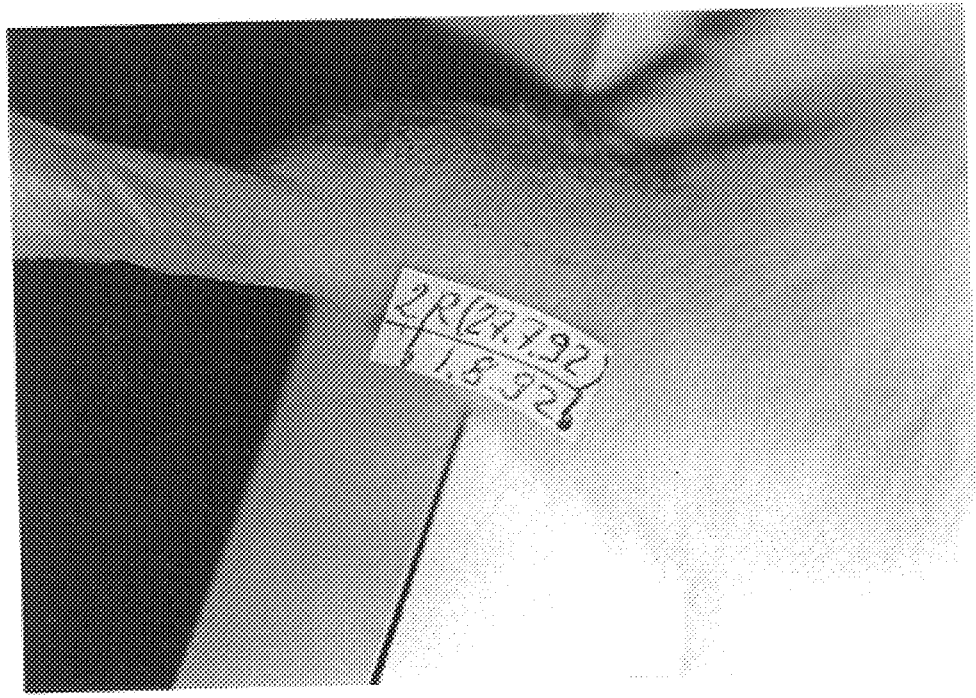
Figure 5:
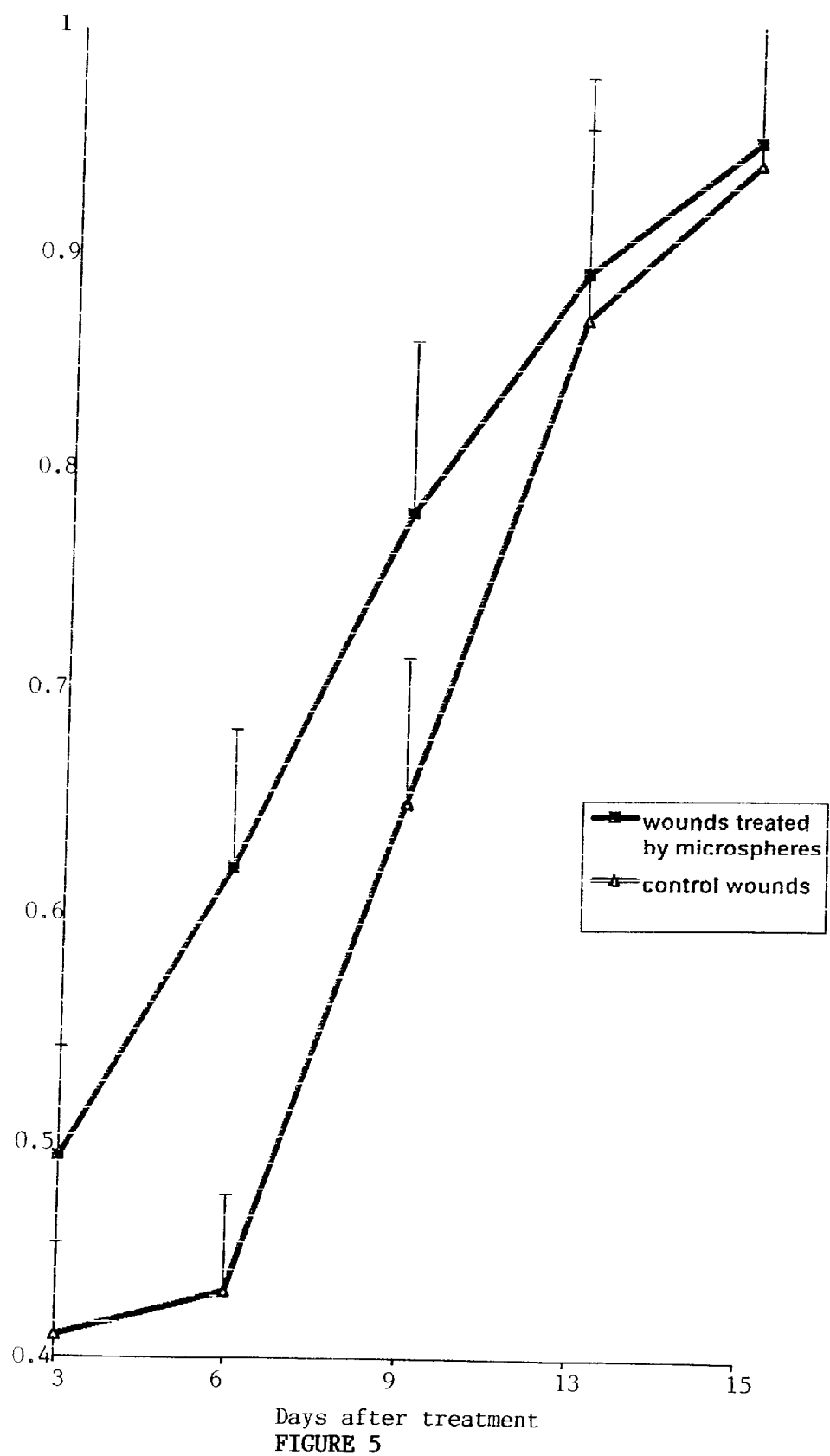
FIG. 5 is a graph at the rate at which wound area of FIG. 4 decreases.

FIGS. 4A–4D show pictures of wound areas prepared as described above. FIG. 4A shows the wound of the control rat immediately after injury, while FIG. 4B shows the equivalent wound of the rat to be treated. FIGS. 4C and 4D show the same rats five days after injury. The wound of the control rat was treated with saline alone, and still has not completely healed. By contrast, the wound of the treated rat, treated with microspheres, has completely healed. Thus, clearly the microspheres of the present invention promote faster wound healing.

FIG. 5 further illustrates the promotion of wound healing by the microspheres of the present invention. The wounds of control rats eventually heal, but at a much slower rate than the wounds of treated rats. Thus, the microspheres clearly increase the rate at which the wound area decreases and the wound heals.

Slides were prepared for histological analysis by making a biopsy punch of the wound area. Rats were sacrificed 4, 5, 6, 7, 8, 9, 13 or 14 days after injury and biopsies were taken for histological examination. The number of specialized myogenic cells incorporated into the newly formed or repaired muscle fibers was counted by determining the number of "new" nuclei, which represent activated myogenic cells. The nuclei of these cells are large, basophilic nuclei with dispersed chromatin and can be easily differentiated from the nuclei of existing myoblasts. Results are given in Table 2.

TABLE 2

Promotion of Muscle Regeneration by Microspheres

| Treatment | Post-surgical Day | "New" Nuclei Per Slide | "New" Nuclei Per Field | "New" Nuclei Per Fiber |
|---|---|---|---|---|
| M | 4 | 422 ± 67 | 52.8 ± 22 | 9.5 ± 3.5 |
| C | 4 | 117 ± 37 | 14.6 ± 10 | 5.9 ± 1.4 |
| M | 5 | 350 ± 84 | 43.8 ± 13.5 | 8.6 ± 1.8 |
| C | 5 | 110 ± 31 | 14.1 ± 4.6 | 4.8 ± 1.2 |
| M | 6 | 1221 ± 180 | 94 ± 25 | 11.9 ± 5 |
| C | 6 | 676 ± 120 | 52 ± 11 | 4.9 ± 0.9 |
| M | 7 | 762 ± 110 | 95 ± 51 | 9.4 ± 3.5 |
| C | 7 | 169 ± 47 | 21.1 ± 4.8 | 4.5 ± 0.8 |
| M | 8 | 715 ± 140 | 89.4 ± 36 | 11 ± 2.2 |
| C | 8 | 126 ± 32 | 18.6 ± 12 | 5.2 ± 1.5 |
| M | 9 | 299 ± 75 | 42.7 ± 19 | 7.4 ± 1.3 |
| C | 9 | 235 ± 84 | 33 ± 12 | 6.5 ± 2.8 |
| M | 13 | 747 ± 129 | 53.3 ± 15 | 9.7 ± 1.5 |
| C | 13 | 582 ± 140 | 42 ± 24 | 5 ± 1.7 |
| M | 14 | 665 ± 143 | 83 ± 24 | 9.4 ± 1.9 |
| C | 14 | 491 ± 124 | 61 ± 36 | 5.5 ± 2.7 |

As shown in Table 2, the microspheres of the present invention clearly promoted muscle regeneration, as measured by the number of "new" or incorporated nuclei in muscle fibers. The fact that such measurements were made on histological samples taken from rats treated in vivo also indicates that the microspheres promote muscle regeneration in vivo as well as in vitro.

Figure 6A:
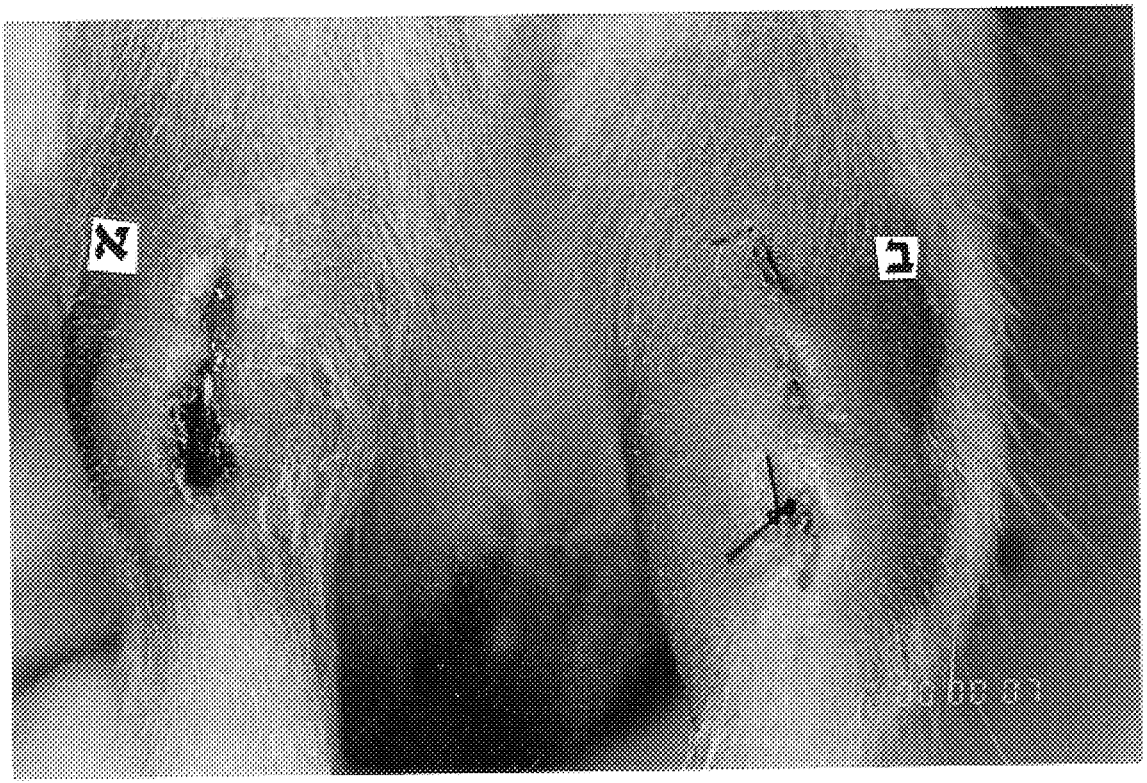
FIGS. 6A and 6B compare the effect of the microspheres of the present invention on wound healing with tissue culture media and saline in rats.
Figure 6B:
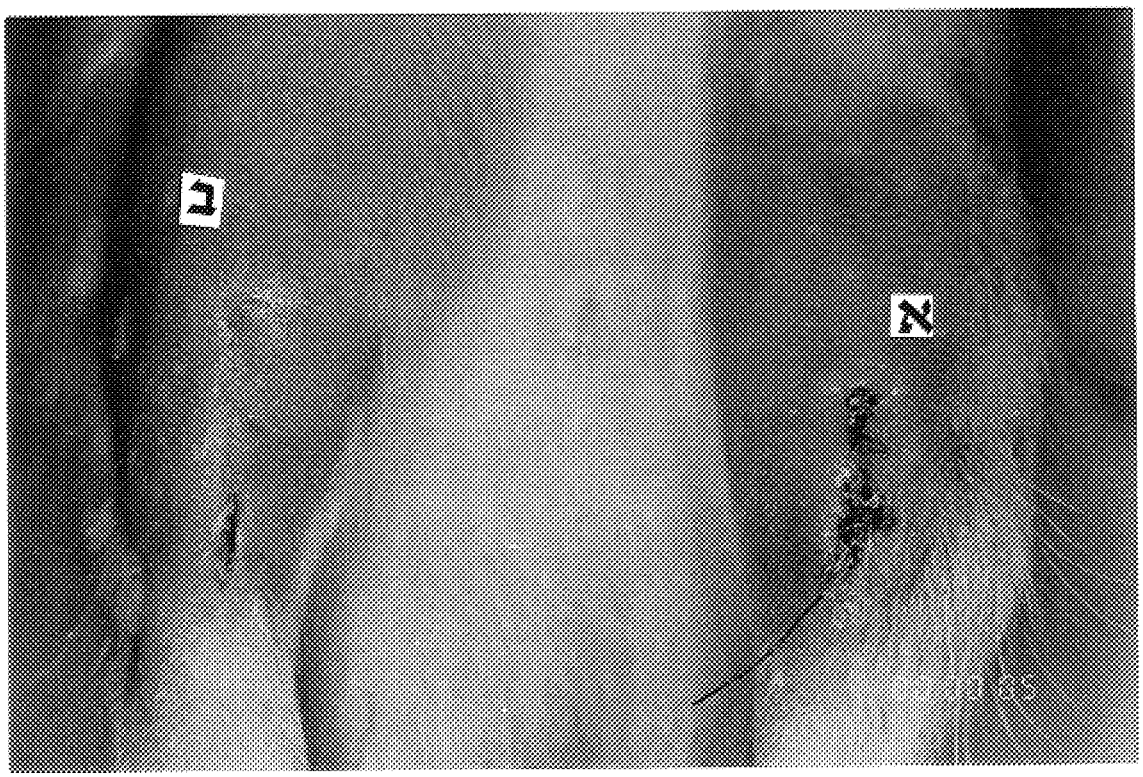

Finally, FIG. 6 compares the effect of the microspheres of the present invention on wound healing with tissue culture media and saline in rats. Wounds were induced in rats as described above, and the rats were treated with saline alone (FIG. 6A, χ), tissue culture media alone (FIG. 6B, χ), saline plus microspheres (FIG. 6A, ]) or tissue culture media plus microspheres (FIG. 6B, ]). The rats were then photographed 4 days after wounding occurred. As can be seen from FIGS. 6A and 6B, the microspheres were able to induce a much more rapid rate of wound healing regardless of whether the carrier was saline or tissue culture media. Thus, tissue culture media was not responsible for any part of the effect of the microspheres of the present invention on wound healing.

EXAMPLE 7

Toxicity Studies of Microspheres

No toxic effect of a preparation containing microspheres was observed. Preliminary examination of treated rats 65 and 180 days after injury showed that none of the following organs exhibited signs of pathological changes: heart, liver, lungs, kidney, blood vessels, stomach, lymph nodes and brain. Experiments with fluorescently-labeled microspheres showed that no signs of pathology were observed in treated rats. Furthermore, the microspheres did not penetrate into any of the above-referenced organs. No new growth was detected in the above-referenced organs. Finally, the microspheres were dispersed within the wound area but did not penetrate into regenerating muscle fibers.

EXAMPLE 8

Effect of Microspheres on Wound Healing in Humans

The in vivo experiments described in Example 6 above clearly demonstrate that the microspheres of the present invention can promote wound healing and muscle regeneration in rats. Furthermore, the results of the toxicity studies in rats described in Example 7 show that the microspheres are substantially non-toxic. Therefore, studies were performed to determine the effect of the microspheres of the present invention on wound healing in humans. As described in detail below, case studies demonstrated that the microspheres clearly promoted wound healing in humans.

Figure 7A:
FIGS. 7A–7D demonstrate the ability of the microspheres of the present invention to promote wound healing in a first human case study.
Figure 7B:
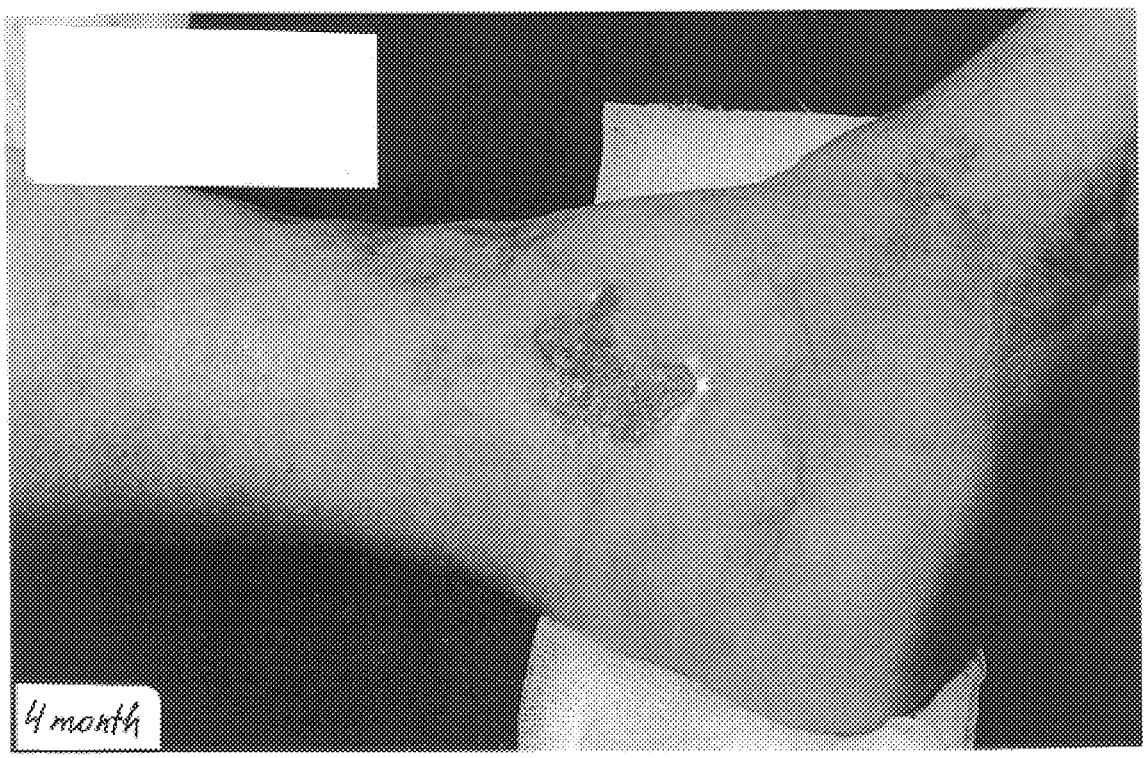
Figure 7C:

The first case study was that of a 66-year old female with ulcers in the left leg which refused to heal. The patient also had cellulitis of the left leg and varicose veins in both legs. Ulcers on the inner thigh of the patient were treated with Milton 2% which is a corrosive chlorine salt in water. Ulcers on the outer thigh of the patient were treated with 4.5 micron microspheres of the present invention made from polystyrene in tissue culture medium. FIG. 7A shows the control wound at day 0, while FIG. 7B shows the control wound after 4 months of treatment. FIG. 7C shows the treated wound at day 0, while FIG. 7D shows the treated wound after 4 months of treatment.

Both the wounds treated with the microspheres of the present invention and those treated with Milton exhibited signs of infection and other difficulties healing during the next four months. However, at the end of the treatment period, the wounds treated with microspheres had shown a significant improvement. The wound size had decreased and the wounds were clean, without signs of infection. Thus, even for wounds which were difficult to heal, due to complications such as infection, the microspheres of the present invention exhibited greater efficacy in wound healing promotion than currently available treatments.

Figure 7D:
Figure 8A:
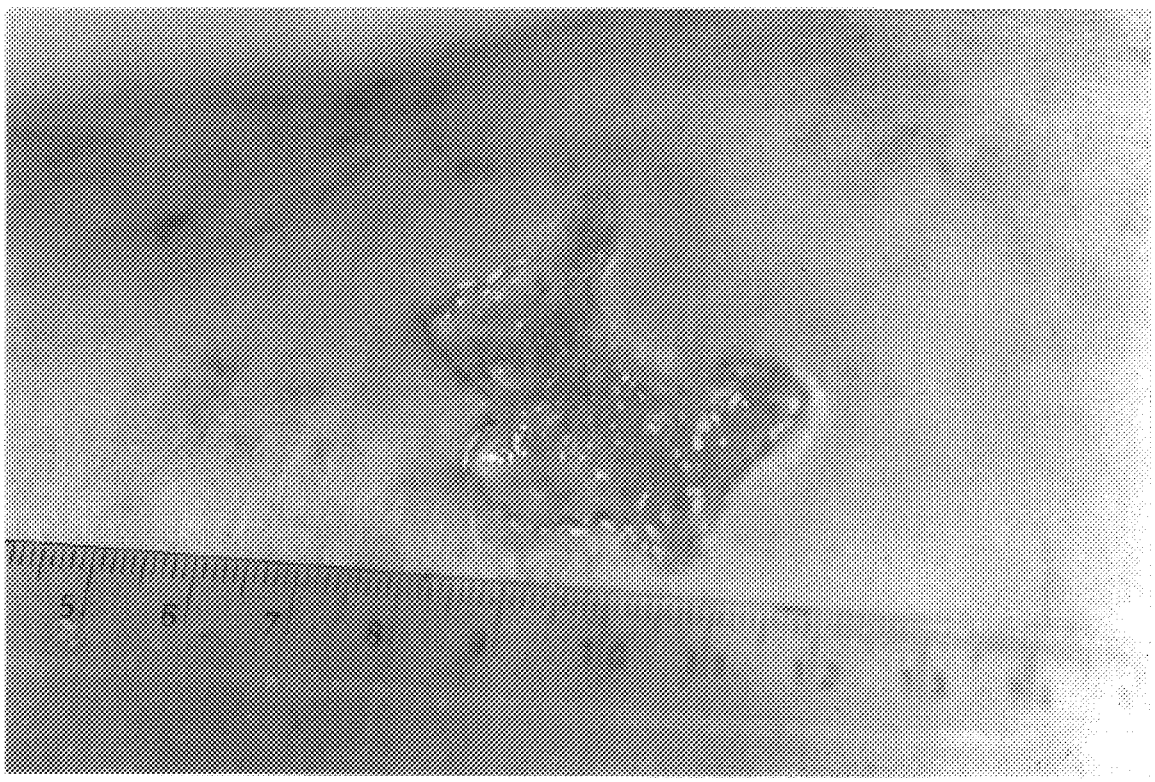
FIGS. 8A and 8B further demonstrate the efficacy of the present invention in the human case study of FIGS. 7A–7D.
Figure 8B:

As a further proof, the wound which had served as a control for FIG. 7 above (FIGS. 7A and 7B) was treated with the same microspheres as those used to treat the wound in FIGS. 7C and 7D. The results are shown in FIGS. 8A and 8B. FIG. 8A shows the wound at day 0 of treatment with microspheres, while FIG. 8B shows the wound after 21 days of treatment. Clearly, the extent of the wound has decreased, even after such a short time period. Furthermore, the wound was superficial and clean, and was no longer producing exudations.

Figure 9A:
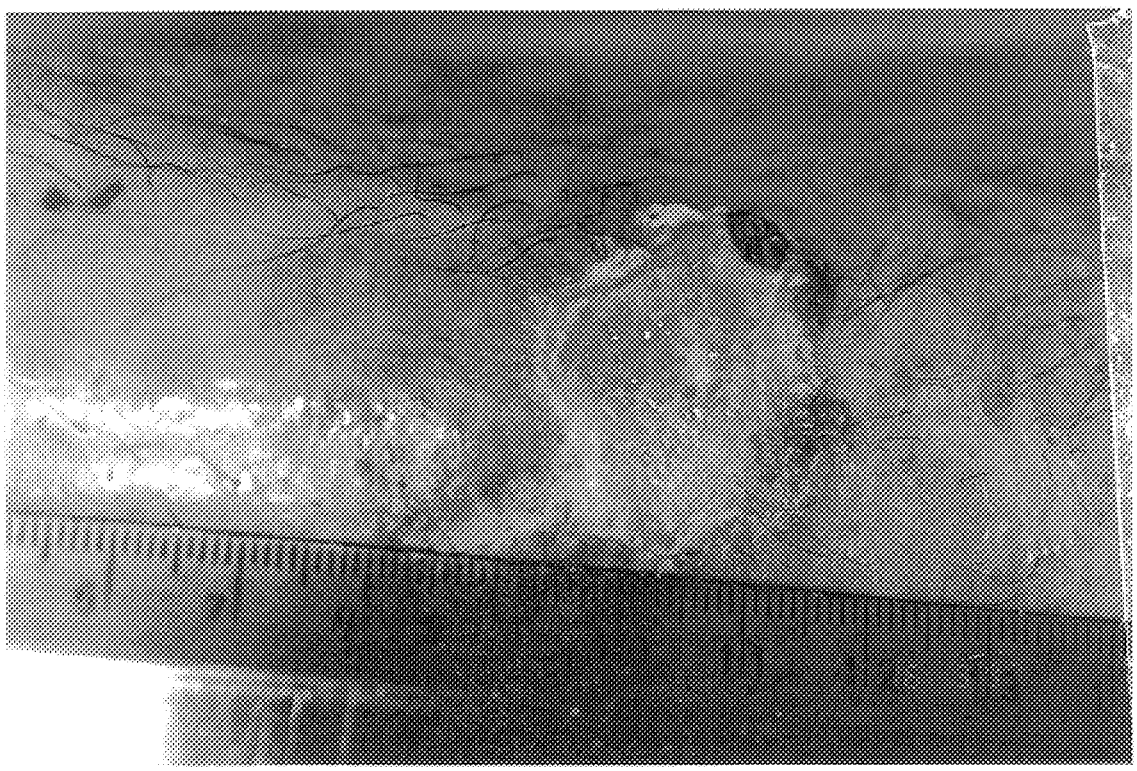
FIGS. 9A and 9B demonstrate the efficacy of the present invention in a second human case study.
Figure 9B:
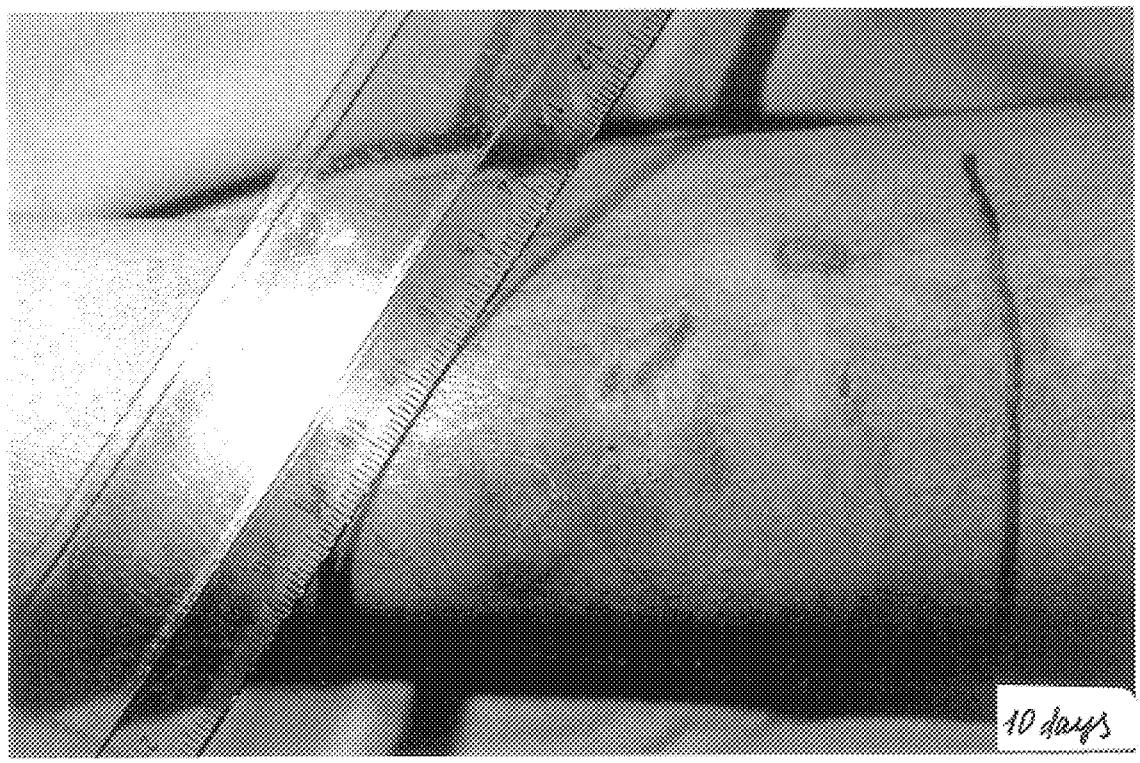

The second case study was that of a 52-year old female who had a year-old infected wound on the front side of the left thigh. The wound was treated with 1% Milton for a week, debrided and then treated with the microspheres of FIGS. 7 and 8 for 10 days. FIG. 9A shows the wound at day 0 of treatment, while FIG. 9B shows the wound after 10 days of treatment.

After 10 days, the wound showed a significant improvement. It had decreased in extent to a small size, was clean and was no longer producing exudations, as can be seen from FIG. 9B. Although the wound did not fully close during the relatively short treatment period, its effects had been significantly ameliorated.

Figure 10A:
FIGS. 10A–10D show the effect of the present invention in a third human case study.
Figure 10B:
Figure 10C:
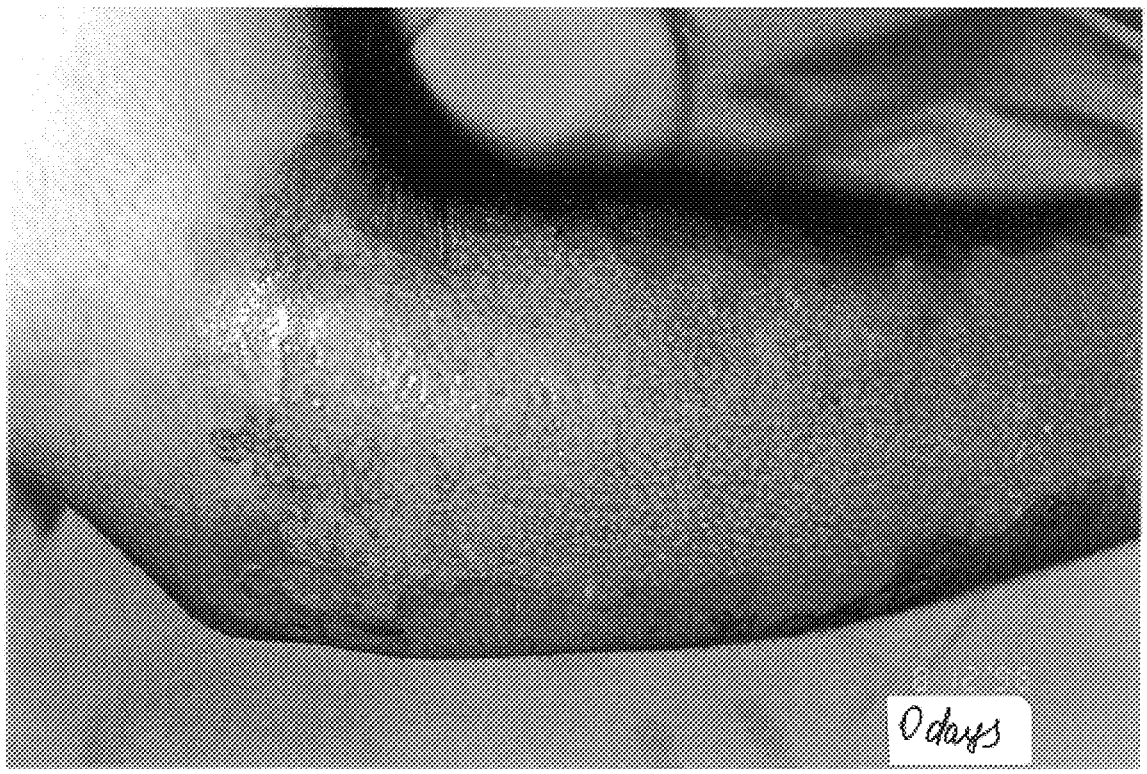
Figure 10D:
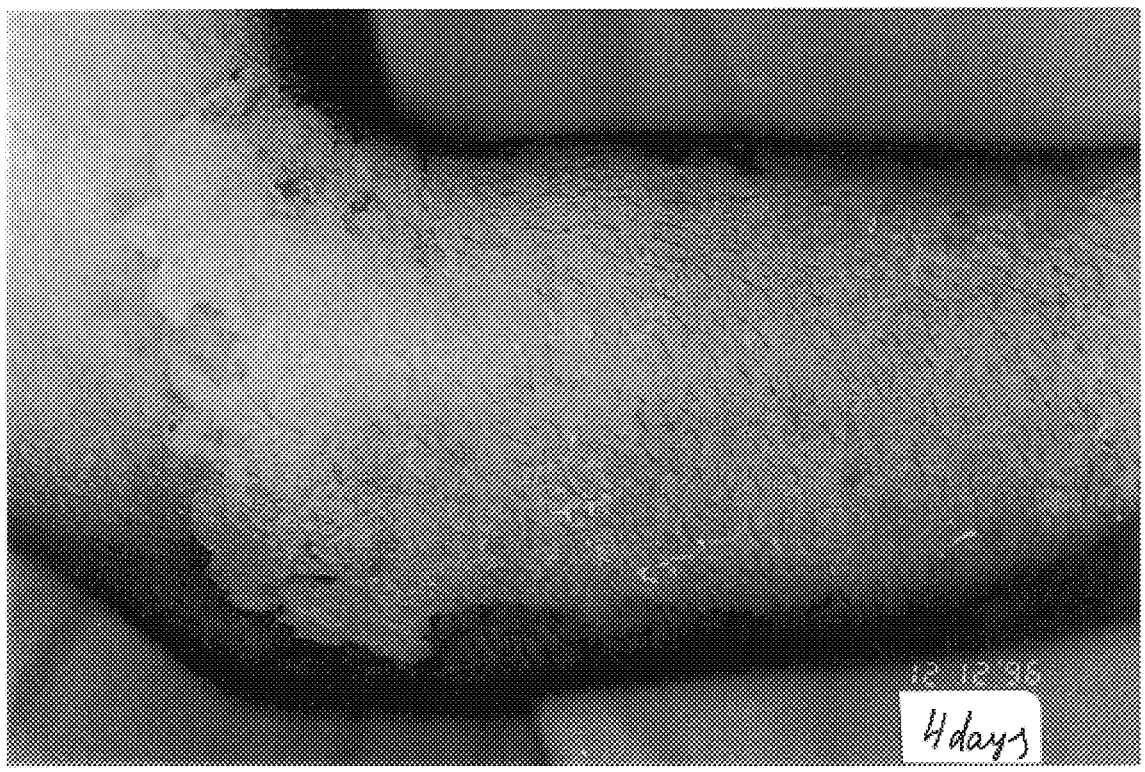

The third case study was that of a 19-year old male who was injured by a chemical spill in an industrial workplace accident. The chemicals in question, sulfurides, caused severe burns and blistering on the right side of his neck and right hand. For the first two days, all wounds were treated with Silverol, a hydrogel with strong absorptive properties. Next, the wounds on the right forearm were treated with the microspheres of case studies 1 and 2, while the remaining wounds were treated with Silverol. The results are shown in FIGS. 10A and 10B (control wound at day 0 and day 5, respectively), and in FIGS. 10C and 10D (treated wound at day 0 and day 5, respectively).

After 5 days of treatment with microspheres, the condition of the treated wound on the forearm had improved significantly over that of the remaining wounds, which were not treated with microspheres. The wound on the forearm had completely healed after 5 days of treatment with microspheres. By contrast, the remaining wounds which were treated with Silverol had not healed completely. Thus, the microspheres clearly promoted wound healing, demonstrating a greater efficacy than currently available treatments.

Figure 11A:
FIGS. 11A and 11B show the efficacy of the present invention in a fourth human case study.
Figure 11B:

The fourth case study was of a 52-year old female who had sustained second-degree burns on the buttocks from a hot bath. Wounds on the left buttock were treated with Silverol, while those on the right buttock were treated with microspheres of the previous case studies. The results are shown, for microsphere-treated wounds only, in FIGS. 11A (day 0) and 11B (day 7) of treatment.

Seven days after beginning treatment, the wounds on the right buttock, which were treated with microspheres, had completely healed with good epithelial growth. By contrast, the wounds on the left buttock, which were treated with Silverol, had not completely healed and were closing relatively slowly. Thus, the microspheres were able to promote wound healing at a more rapid rate than conventional treatments.

The fifth case study was of a 28 year old female who had suffered extensive and severe sunburn (data not shown). She was treated with the microspheres of the previous case studies. The patient reported both a significant reduction in discomfort and rapid healing of the sunburn. Thus, the microspheres used in the method and device of the present invention can both relieve discomfort and promote wound healing, although it should be noted that the relief of discomfort is probably a highly indirect effect of the microspheres rather than direct analgesia.

Indeed, it is worth mentioning that the above patient report can only be inferred to include the apparent reduction in the sensation of discomfort from the sunburn. Such decreased discomfort probably does not demonstrate any ability of the microspheres to have a direct effect on the transmission of nerve impulses, or indeed to directly alter any of the many factors which lead to the sensation of discomfort. Instead, this effect is probably highly indirect, occurring as a result of the activation of macrophages, which in turn has anti-inflammatory effects, leading to the decreased sensation of discomfort by the patient.

From these five case histories, coupled with the extensive evidence obtained from studies in rats, the use of the agents, such as microspheres, according to the present invention has clearly been shown to have greater efficacy for the promotion of wound healing and muscle regeneration than currently available, prior art treatments. The method and device promotes, accelerates and enhances wound healing, as well as diminishing discomfort experienced by the subject.

With regard to the diminished discomfort, it should be noted that the patients in the above case studies also reported local reduction in pain and discomfort from the treated wounds, particularly the patient suffering from sunburn, probably an indirect effect of the microspheres through their (also indirect) anti-inflammatory action.

Finally, although the data is not shown, an indirect bacteriostatic effect against infections of the wounds by Pseudomonas species was also noted in humans. The mechanism for both the indirect anti-inflammatory action and the indirect bacteriostatic effect is not clear, but is probably a result of a cellular effect involving the attraction and activation of macrophages. Regardless of the exact mechanism, the use of the microspheres according to the present invention clearly represents a significant improvement in the treatment of wounds.

It will be appreciated that the above descriptions are intended only to serve as examples, and that many other embodiments arc possible within the spirit and the scope of the present invention.

What is claimed is:

1. A method of treating a wound of a subject, comprising the step of administering a composition to the wound of the subject, said composition consisting essentially of a microsphere being capable of forming a multi-point contact with a cellular membrane, said microsphere being substantially non-biodegradable during the period of treament, said microsphere being made from a material selected from the group consisting of polystyrene, polystyrene derivatized with a moiety selected from the group consisting of amino and carboxyl, polylysine, poly-N-ethyl-4-vinylpyridinium bromide, polymethylacrylate and silicone, and said material of said microsphere featuring a surface group with a substantial charge.

2. The method of claim 1, wherein said microsphere is made from a material selected from the group consisting of polystyrene and polystyrene derivatized with a moiety selected from the group consisting of amino and carboxyl.

3. The method of claim 1, wherein said surface group is selected from the group consisting of sulfate, protamine, protamine sulfate, protamine salts, and carboxyl.

4. The method of claim 3, wherein said surface group is selected from the group consisting of carboxyl.

5. The method of claim 1, wherein said microsphere has a diameter in a range of from about 0.01 microns to about 200 microns.

6. The method of claim 5, wherein said microsphere has a diameter in a range of from about 0.1 microns to about 100 microns.

7. The method of claim 6, wherein said microsphere has a diameter in a range of from about 0.1 micros to about 20 microns.

8. The method of claim 1, wherein said composition further comprises a pharmaceutically acceptable carrier for said microsphere, said microsphere being substantially insoluble in said carrier.

9. The method of claim 1, wherein the wound is selected from the group consisting of burn, trauma, post-surgical, post-childbirth and chronic.

10. The method of claim 9, wherein said burn wound is selected from the group consisting of sunburn, chemical burn, radiation burn and thermal burn.

11. The method of claim 9, wherein said chronic wound is selected from the group consisting of bedsores, pressure sores, diabetes-related and poor circulation-related.

12. The method of claim 1, wherein the wound is located on a potion of the body of the subject selected from the group consisting of skin and muscle.

* * * * *